United States Patent
Zamanzadeh et al.

(10) Patent No.: US 11,009,448 B2
(45) Date of Patent: May 18, 2021

(54) ATMOSPHERIC CORROSIVITY MAPPING METHOD AND APPARATUS

(71) Applicant: MATERGENICS, INC., Pittsburgh, PA (US)

(72) Inventors: Mehrooz Zamanzadeh, Pittsburgh, PA (US); Peyman Taheri Bonab, Vancouver (CA); Carolyn Tome, Pittsburgh, PA (US); Alyson Char, Vancouver (CA)

(73) Assignee: Matergenics, Inc.

( * ) Notice: Subject to any disclaimer, the term of this patent is extended or adjusted under 35 U.S.C. 154(b) by 0 days.

(21) Appl. No.: 17/065,559

(22) Filed: Oct. 8, 2020

(65) Prior Publication Data
US 2021/0109009 A1    Apr. 15, 2021

Related U.S. Application Data

(60) Provisional application No. 62/913,760, filed on Oct. 11, 2019.

(51) Int. Cl.
*G01N 17/00*    (2006.01)
*G01W 1/00*    (2006.01)
(Continued)

(52) U.S. Cl.
CPC .............. *G01N 17/00* (2013.01); *G01W 1/00* (2013.01); *G06F 16/2264* (2019.01); *G06F 16/29* (2019.01)

(58) Field of Classification Search
CPC ...... G06F 16/2264; G06F 16/29; G01W 1/00; G01N 17/00; G01N 17/02
See application file for complete search history.

(56) References Cited

U.S. PATENT DOCUMENTS 6,243,483 B1   6/2001   Petrou et al.
8,412,419 B1   4/2013   Seamon et al.
(Continued)

FOREIGN PATENT DOCUMENTS

CN    102903132 A      1/2013
CN    106483060 A  *  3/2017
(Continued)

OTHER PUBLICATIONS

Masetti, University of New Hampshire Scholars' Repository, 101-200 (Year: 2012).*
(Continued)

*Primary Examiner* — Alexander Satanovsky
*Assistant Examiner* — Lynda Dinh
(74) *Attorney, Agent, or Firm* — Thomas M. Joseph, Esq.

(57) ABSTRACT

A plurality of disparate datasets is aggregated into a geodata data structure specifying a plurality of geospatial locations and a set of aspatial parameters at each geospatial location. Each aspatial parameter is combined at each geospatial location to generate an atmospheric corrosivity scale parameter at each of the plurality of geospatial locations. A grid is created with cells representing each of the plurality of geospatial locations and each of the corresponding atmospheric corrosivity scale parameters. The grid is stored for output of at least a portion of the plurality of geospatial locations and the corresponding atmospheric corrosivity scale parameters overlaid on a geographic map.

6 Claims, 5 Drawing Sheets

(51) Int. Cl.
      *G06F 16/29*       (2019.01)
      *G06F 16/22*       (2019.01)

(56) References Cited

U.S. PATENT DOCUMENTS

| | | |
|---|---|---|
| 9,928,319 B1 | 3/2018 | Dow et al. |
| 10,107,770 B2 | 10/2018 | Weindorf et al. |
| 2012/0279599 A1 | 11/2012 | Gluskin et al. |
| 2015/0185133 A1 | 7/2015 | Murray |
| 2015/0268152 A1* | 9/2015 | Friedersdorf ...... G01N 33/0031 73/25.01 |
| 2016/0370333 A1* | 12/2016 | Li ...................... G01N 33/0004 |
| 2017/0030850 A1 | 2/2017 | Castaneda-Lopez et al. |
| 2017/0316846 A1 | 11/2017 | Efraimsson et al. |
| 2017/0350807 A1* | 12/2017 | Minamitani ........... G01N 17/00 |
| 2018/0238820 A1 | 8/2018 | Ghods et al. |
| 2020/0128720 A1 | 4/2020 | Cizek |

FOREIGN PATENT DOCUMENTS

| | | | |
|---|---|---|---|
| CN | 107403265 | * | 11/2017 |
| CN | 108020501 A | * | 5/2018 |

OTHER PUBLICATIONS

ArcGIS Desktop, "What is Geodata?" (Year: 2016).*
Masetti, University of New Hampshire Scholars' Repository, pp. 1-100 (Year: 2012).*
Masetti, University of New Hampshire Scholars' Repository, pp. 201-286 (Year: 2012).*
Google translation of CN102903132, Jan. 30, 2013.
ISO 9223, Second Edition Feb. 1, 2012.

* cited by examiner

ATMOSPHERIC CORROSIVITY MAPPING METHOD AND APPARATUS

CROSS REFERENCE TO RELATED APPLICATION

This application claims the benefit under 35 U.S.C. § 119(e) of U.S. Provisional Application No. 62/913,760 entitled "ATMOSPHERIC CORROSIVITY MAPPING METHOD AND APPARATUS" filed Oct. 11, 2019, which is incorporated herein by reference.

BACKGROUND

Atmospheric corrosion can affect bridges, flag poles, buildings, monuments and other outdoor objects. Economic losses caused by atmospheric corrosion are enormous and results in the disappearance of a significant portion of metal produced. Atmospheric corrosion has been reported to account for more failures in terms of cost and tonnage than any other type of material degradation processes.

Certain atmospheres can be particularly corrosive environments. A large portion of the damage caused by corrosion is attributed to atmospheric corrosion. Protective coatings and, in particular, metals are subject to deterioration when exposed to atmospheric environments. Other materials can be adversely affected by such corrosive environments, as well. Accordingly, there is a need for improved tools for prioritization of atmospheric corrosion inspections, predicting corrosion rate, and monitoring corrosion risk.

SUMMARY

The following summary is provided to introduce a selection of concepts in a simplified form that are further described below in the detailed description. This summary is not intended to identify key features or essential features of the claimed subject matter, nor is it intended to be used to limit the scope of the claimed subject matter.

In various implementations, a plurality of disparate datasets is aggregated into a geodata data structure specifying a plurality of geospatial locations and a set of aspatial parameters at each geospatial location. Each aspatial parameter is combined at each geospatial location to generate an atmospheric corrosivity scale parameter at each of the plurality of geospatial locations. A grid is created with cells representing each of the plurality of geospatial locations and each of the corresponding atmospheric corrosivity scale parameters. The grid is stored for output of at least a portion of the plurality of geospatial locations and the corresponding atmospheric corrosivity scale parameters overlaid on a geographic map.

In other implementations, datasets having aspatial data corresponding to a plurality of geospatial locations from a plurality of data sources are imported. The datasets are stored in a plurality of file attribute tables with the aspatial data linked to the corresponding plurality of geospatial locations within the plurality of file attribute tables. A plurality of data layers is aggregated from the plurality of file attribute tables to determine an atmospheric corrosivity scale parameter at each of the plurality of geospatial locations. A grid with cells representing each of the plurality of geospatial locations and the corresponding atmospheric corrosivity scale parameters is created. The grid is stored for output of at least a portion of the plurality of geospatial locations and the corresponding atmospheric corrosivity scale parameters overlaid on a geographic map.

These and other features and advantages will be apparent from a reading of the following detailed description and a review of the appended drawings. It is to be understood that the foregoing summary, the following detailed description and the appended drawings are explanatory only and are not restrictive of various aspects as claimed.

DETAILED DESCRIPTION

Figure 1:
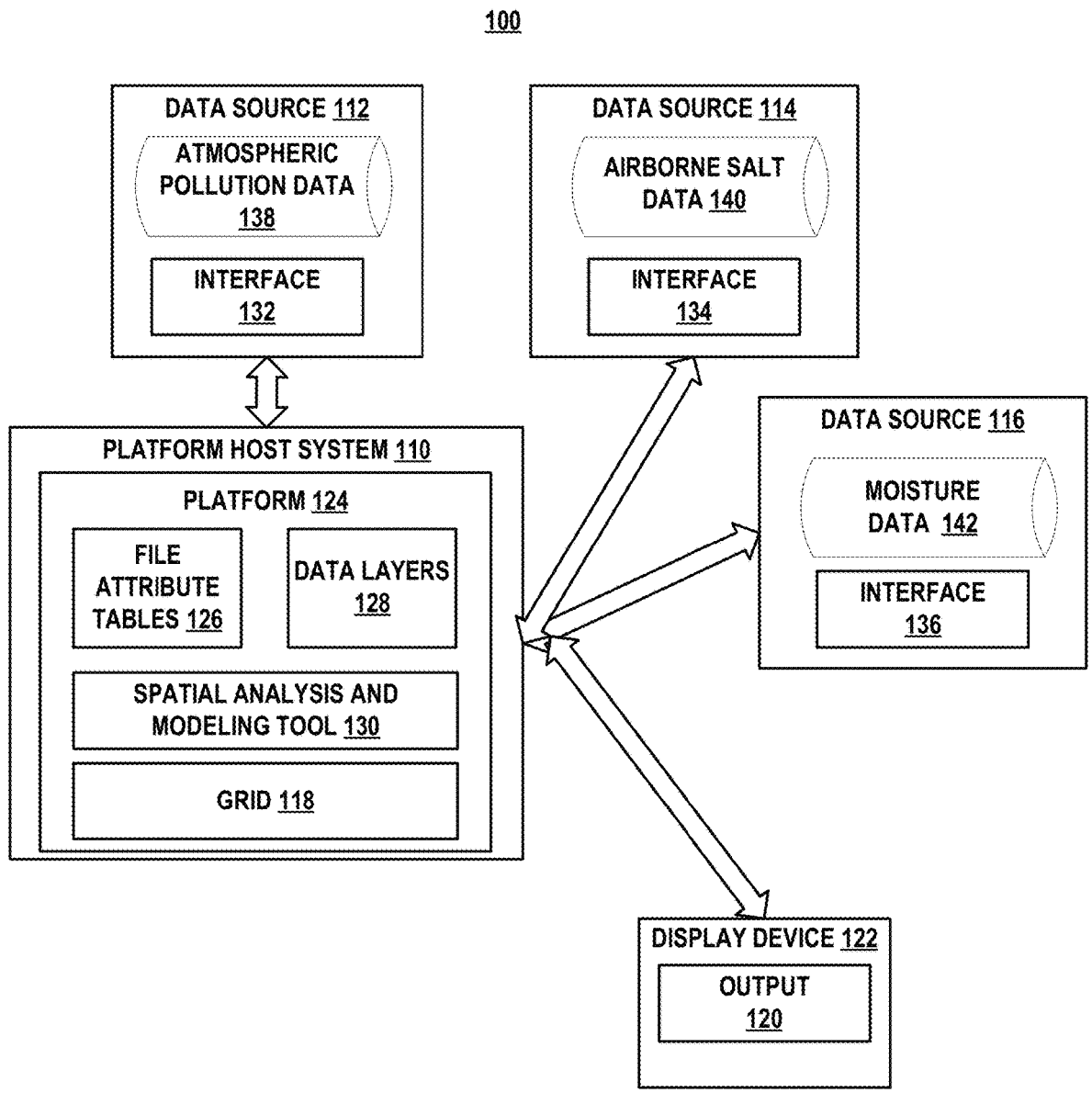
FIG. 1 is a schematic diagram of an operating environment in accordance with the subject disclosure.

The subject disclosure is directed to methods and apparatus for generating corrosivity maps, and, more particularly, to systems that generate atmospheric corrosion risk assessment maps to help asset owners identify areas of high, medium and low below-ground corrosion risks. The systems aggregate data relating to various properties of the atmosphere to identify the areas of high, medium, and low atmospheric corrosivity. As a result, users can deploy its resources to specific areas of highest corrosion risk in a more efficient manner.

The detailed description provided below in connection with the appended drawings is intended as a description of examples and is not intended to represent the only forms in which the present examples can be constructed or utilized. The description sets forth functions of the examples and sequences of steps for constructing and operating the examples. However, the same or equivalent functions and sequences can be accomplished by different examples.

References to "one embodiment," "an embodiment," "an example embodiment," "one implementation," "an implementation," "one example," "an example" and the like, indicate that the described embodiment, implementation or example can include a particular feature, structure or characteristic, but every embodiment, implementation or example can not necessarily include the particular feature, structure or characteristic. Moreover, such phrases are not necessarily referring to the same embodiment, implementation or example. Further, when a particular feature, structure or characteristic is described in connection with an embodiment, implementation or example, it is to be appreciated that such feature, structure or characteristic can be implemented in connection with other embodiments, implementations or examples whether or not explicitly described.

Numerous specific details are set forth in order to provide a thorough understanding of one or more embodiments of the described subject matter. It is to be appreciated, however, that such embodiments can be practiced without these specific details.

Various features of the subject disclosure are now described in more detail with reference to the drawings, wherein like numerals generally refer to like or corresponding elements throughout. The drawings and detailed description are not intended to limit the claimed subject matter to the particular form described. Rather, the intention is to cover all modifications, equivalents and alternatives falling within the spirit and scope of the claimed subject matter.

The subject disclosure is directed to systems and methods for generating atmospheric corrosivity maps. The corrosion maps determine the relative corrosivity of a particular region based on atmospheric pollution, atmospheric salinity, and moisture. These factors can be considered with respect to wind loads. The phrases "corrosivity map" and "corrosion risk map" shall be used interchangeably herein.

The corrosivity maps can be produced by combining data using geo-statistical techniques and modeling. The specific environmental conditions that affect the source and distribution of airborne salinity will also be considered in construction of corrosion risk maps.

The maps can be produced in two phases. In the first phase, relevant data is collected, categorized, and analyzed. The information can include several distinctive sets of data such as chloride deposition rates, sulfate deposition rates, time of wetness and wind data. In the second phase, the data is verified.

Referring to FIG. 1, various features of the subject disclosure are now described in more detail with respect to an operating environment, generally designated with the numeral 100, for generating atmospheric corrosivity maps. The operating environment 100 includes a platform host system 110 that aggregates data from a variety of sources 112-116 and stores the data in a geodata data structure. The data includes geospatial locations and linked aspatial parameters. The platform host system 110 utilizes the data to generate corrosivity scale parameters at each of the geospatial locations by weighing the aspatial parameters and uses the data to create a grid 118 of cells. The grid 118 is stored for output 120 on a display device 122 as an atmospheric corrosivity map.

The platform host system 110 can include a platform 124 that utilizes the grid 118, file attribute tables 126, data layers 128, and a spatial analysis and modeling tool 130. The platform host system 110 stores the data within the file attribute tables 126 and aggregates the data into data layers 128. The platform host system 110 assigns a weight to each of data layers 128 to form weighted data layers for generating corrosivity scale parameters linked to various locations within a predetermined geographic area. In this exemplary embodiment, the spatial analysis and modeling tool 130 can be a spatial analyst toolbox that assigns weighting to layers based upon importance.

The platform host system 110 and the platform 124 can comprise hardware, software, and data that collect, sort, analyze, and disseminate information about the Earth. The platform host system 110 and the platform 124 integrates various disciplines and technologies, such as remote sensing, cartography, surveying, and computer science. The system can assist users in finding the least corrosive sites, the most corrosive sites, access to sites, locate corrosive environments for corrosion risk mitigation.

The platform 124 can use Geographic Information System (GIS) software, such as the Aeronautical Reconnaissance Coverage Geographic Information System (ArcGIS), Google Earth, Google Maps, and AutoCAD MAP. In this exemplary embodiment, the platform 124 is ArcGIS, which represents a suite of products such as ArcMAP and Arc Catalog, which provides software tools for visualizing and analyzing data. ArcMAP can be used to display and to explore ArcGIS datasets.

The platform host system 110 communicates with the sources 112-116 through interfaces 132-136. The source 112 stores atmospheric pollution data 138. The atmospheric pollution data 138 can relate to sulfur dioxide pollution, which is a major cause of atmospheric corrosion that is more prevalent in industrial and urban environments.

Sulfur dioxide is a colorless gas, belonging to the family of gases called sulfur oxides. Sulfur dioxide reacts on the surface of a variety of airborne solid particles, is soluble in water and can be oxidized within airborne water droplets. Sulfur dioxide, a product of the combustion of sulfur containing fossil fuels, plays an important role in atmospheric corrosion in urban and industrial type atmospheres.

Sulfur dioxide can be adsorbed on metal surfaces, has a high solubility in water and tends to form sulfuric acid (acid rain) in the presence of moisture films. Sulfate ions are formed in the surface moisture layer by the oxidation of sulfur dioxide and their formation is considered to be the main corrosion accelerating effect from sulfur dioxide.

The source 114 stores airborne salt data 140 relating to atmospheric salinity and atmospheric chloride content. Chlorides are a major component of most salts, which accelerate corrosion due to their hydrophilic nature. Chlorides can produce highly conductive electrolytes.

Chlorides are a main catalyst for pitting corrosion, which is an autocatalytic, localized attack. Chlorides are known to cause hydrolysis and create acidic chlorides. In addition, corrosion products that contain chlorides are typically more soluble than those that contain oxides.

The airborne salt data 140 can be obtained by monitoring airborne salts carried by the wind from the ocean. Airborne salt data is especially important with respect to the initiation and propagation of localized corrosion damage under the influence of chloride ions. Airborne chloride concentrations are not monitored by weather stations and the models that we use to determine them are only accurate up to a few miles from the shore.

The airborne salt data 140 affects atmospheric corrosion rates by enhancing surface electrolyte formation by hygroscopic action and through the direct participation of chloride ions in the electrochemical corrosion reactions is likely.

Chloride salts can cause pitting and crevice corrosion in passivating alloys, such as stainless steel, aluminum alloys and titanium alloys. In ferrous alloys, iron chloride complexes tend to be unstable (soluble), resulting in further stimulation of corrosive attack. Chloride salts tend to be less soluble in other metals, such as zinc and copper. Such metals can display lower chloride induced corrosion rates.

The source 116 stores moisture data 142, which can relate to time of wetness measurements. The time of wetness is a measure of how much time the material will be in contact with a conducting solution. Wet surfaces are caused by factors such as dew, rainfall, melting snow, or high humidity. These conditions are estimated by looking at the time during which the relative humidity is greater than 80% at temperatures greater than 0° C.

The time of wetness of a corroding surface is a key parameter, directly determining the duration of the electrochemical corrosion processes. It is a complex variable that relates to means of formation and evaporation of the surface electrolyte solution. The time of wetness can refer to the period of time during which the atmospheric conditions are favorable for the formation of a surface layer of moisture on a metal or alloy.

The surface layer can form a moisture film that relates to various chemical mechanisms of the corrosion process. In some embodiments, the time of wetness can be the time period during which the relative humidity is in excess of 80% and the temperature is above 0 degrees Celsius. In such embodiments, time of wetness can be determined from weather data or measured directly through various means.

It should be understood that one or more of the data sources 112-116 can communicate with the platform host system 110 over an electronic network, but such communication is not necessary for the data sources 112-116 to share information with the platform host system 110. Additionally, the platform host system 110 can communicate with the display device 122 over the network, but the use of a network is not necessary for such communication.

The electronic network can be implemented by any type of network or combination of networks including, without limitation: a wide area network (WAN) such as the Internet, a local area network (LAN), a Peer-to-Peer (P2P) network, a telephone network, a private network, a public network, a packet network, a circuit-switched network, a wired network, and/or a wireless network. Servers and workstations can communicate via networks using various communication protocols (e.g., Internet communication protocols, WAN communication protocols, LAN communications protocols, P2P protocols, telephony protocols, and/or other network communication protocols), various authentication protocols, and/or various data types (web-based data types, audio data types, video data types, image data types, messaging data types, signaling data types, and/or other data types).

The platform host system 110 can identify areas at higher risk for corrosion. The platform host system 110 can produce an atmospheric corrosion risk assessment map for areas of high corrosion risk as output 120. Such atmospheric corrosion risk assessment maps or corrosivity maps can combine various properties of the atmosphere to identify areas of high, medium, and low atmospheric corrosivity.

Figure 2:
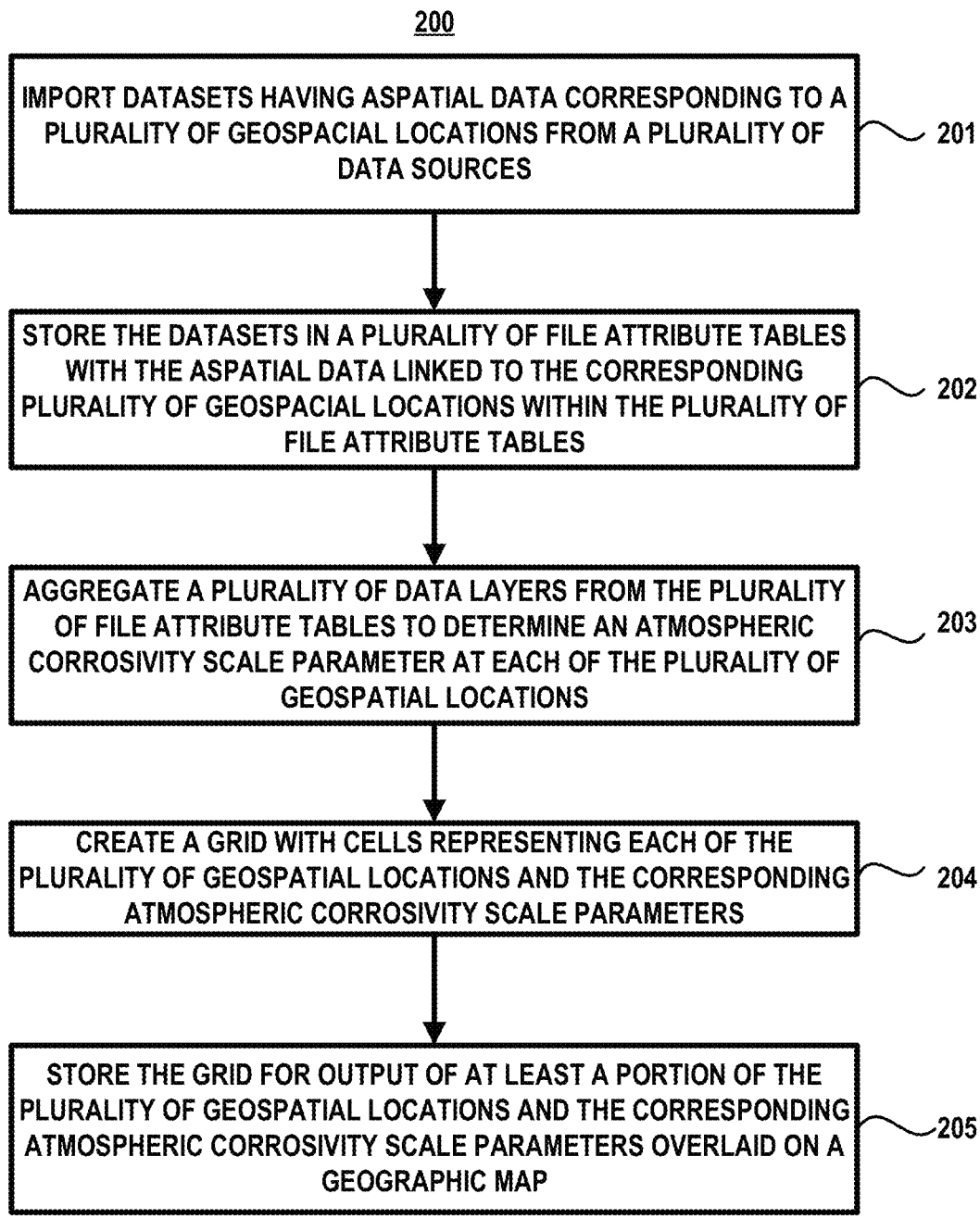
FIG. 2 is an exemplary process in accordance with the subject disclosure.

Referring to FIG. 2 with continuing reference to the foregoing figures, an exemplary process, generally designated by the numeral 200, for generating atmospheric corrosivity maps is shown. In this exemplary embodiment, the process 200 can be performed by the operating environment 100 shown in FIG. 1.

At 201, datasets having aspatial data corresponding to a plurality of geospatial locations are imported from a plurality of data sources. In this exemplary embodiment, the data sources can be the sources 112-116 shown in FIG. 1. The aspatial data can include data relating to pollution, airborne salt content, and moisture. More specifically, the data can include data relating to sulfur dioxide pollution, chloride deposition and time of wetness.

The data sources 112-116 can include two types of data, such as spatial data and aspatial data. Spatial data can be in the form of graphics and/or data in a map. Spatial data can include vectors (i.e., lines, polygons, points, etc.). Raster data includes gridded data, which can represent discrete objects as collections of cells and/or fields by assigning attribute value to cells.

At 202, the datasets are stored in a plurality of file attribute tables with the aspatial data linked to the corresponding plurality of geospatial locations within the plurality of file attribute tables. In this exemplary embodiment, the file attribute tables can be the file attribute tables 126 shown in FIG. 1. The file attribute tables 126 can include a polygon file attribute table, a component file attribute table, and other similar file attribute tables. The tables can be linked to an original polygon file through unique ID numbers.

At 203, a plurality of data layers is aggregated from the plurality of file attribute tables to determine an atmospheric corrosivity scale parameter at each of the plurality of geospatial locations. In this exemplary embodiment, the data layers can be the data layers 128 shown in FIG. 1.

In some exemplary embodiments, the aspatial parameters are combined to generate each atmospheric corrosivity scale parameter using a predetermined formula. In other exemplary embodiments, the system iterates through the geodata data structure to assign weights to each aspatial parameter at each geospatial location and generates an atmospheric corrosivity scale parameter at each of the plurality of geospatial locations based upon the weight of each aspatial parameter at each of the plurality of geospatial locations. The weights can be assigned using the spatial analysis and modeling tool 130.

The data layers 128 are converted into weighted data layers that are defined on a common scale. The common scale can be a dimensionless scale of 1-9 with 1-3 representing the least corrosive, 4-6 representing moderately corrosive, and 7-9 representing the most corrosive. The platform 124 shown in FIG. 1 can identify the various layers as necessary layers and unnecessary layers. In some embodiments, the scale can be based on the corrosivity categories C1-CX set forth in International Standard ISO 9223.

At 204, a grid with cells representing each of the plurality of geospatial locations and the corresponding atmospheric corrosivity scale parameters is created. In this exemplary embodiment, the grid can be the grid 118 shown in FIG. 1.

At 205, the grid is stored for output of at least a portion of the plurality of geospatial locations and the corresponding atmospheric corrosivity scale parameters overlaid on a geographic map. In this exemplary embodiment, the output can be the output 120 shown in FIG. 1. The output 120 can be displayed on the display device 122 shown in FIG. 1. The corrosion maps represent a combination of data relating to atmospheric pollution, atmospheric salinity, and moisture.

Exemplary Output

Figure 3:
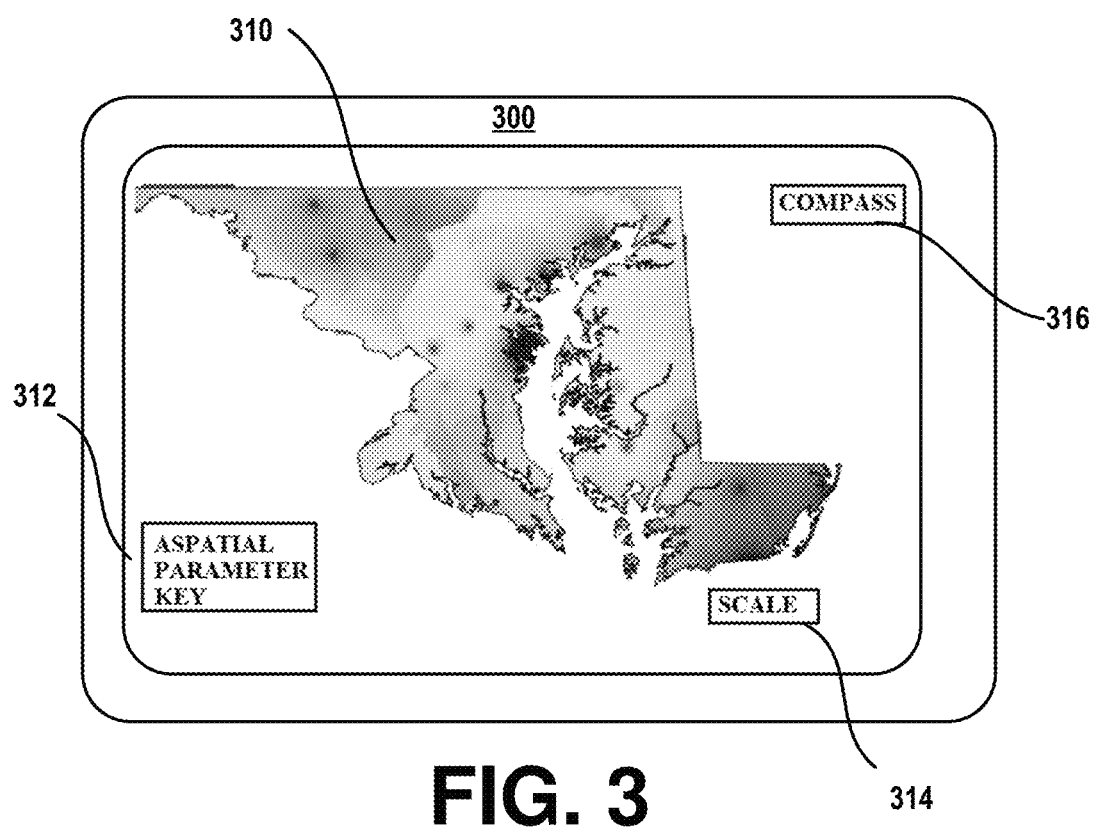
FIG. 3 is a top plan view of a display device illustrating exemplary output in accordance with the subject disclosure.

Referring to FIG. 3 with continuing reference to the foregoing figures, a display device, generally designated with the numeral 300, which is configured to display exemplary output in accordance with the subject disclosure, is shown. In this exemplary embodiment, the display device 300 can be the display device 122 shown in FIG. 1.

As shown in FIG. 3, the display device 300 can display exemplary output 310 in the form of a representation of an atmospheric corrosivity map. The display device 300 can also display a map key in the form of an aspatial parameter key 312, a scale 314, and a compass 316 that indicates compass directions for the atmospheric corrosivity map. The exemplary output 312 can represent intermediate output representing one of the data layers 128 shown in FIG. 1 and produced at Step 203 shown in FIG. 2.

Exemplary Processes

Figure 4:
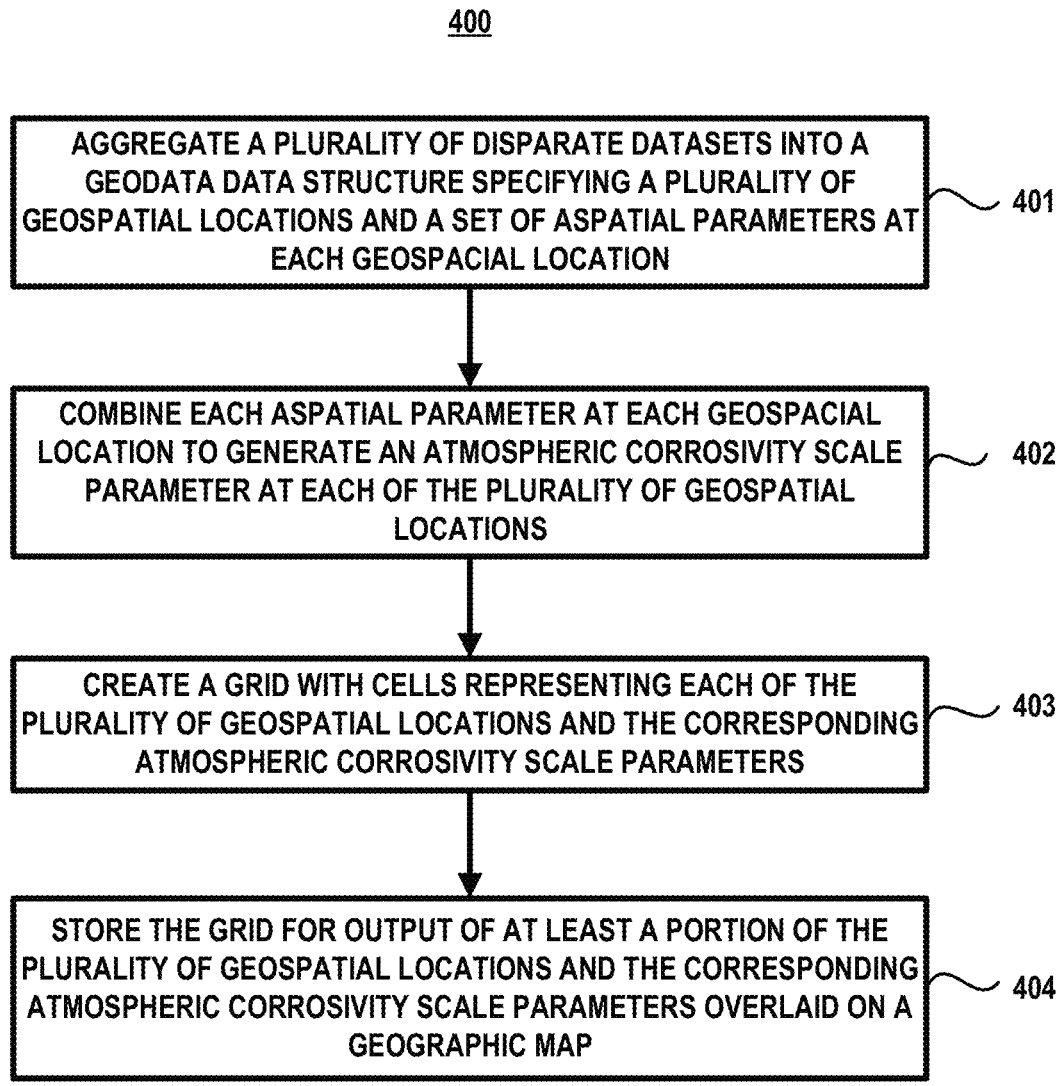
FIG. 4 is another exemplary process in accordance with the subject disclosure.

Referring to FIG. 4 with continuing reference to the foregoing figures, an exemplary process, generally designated by the numeral 400, for generating atmospheric corrosivity maps is shown. In this exemplary embodiment, the process 400 can be performed by the operating environment 100 shown in FIG. 1.

At 401, a plurality of disparate datasets is aggregated into a geodata data structure specifying a plurality of geospatial locations and a set of aspatial parameters at each geospatial location. In this exemplary embodiment, the disparate datasets are stored with data sources 112-116 shown in FIG. 1.

At 402, each aspatial parameter is combined at each geospatial location to generate an atmospheric corrosivity scale parameter at each of the plurality of geospatial locations, In some embodiments, the aspatial parameters are combined to determine each corrosivity scale parameter using a predetermined formula. In other embodiments, Step 402 is performed by assigning a weight to each of the plurality of data layers to form a plurality of weighted data layers and combining the weighted data layers to generate an atmospheric corrosivity scale parameter at each of the plurality of geospatial locations.

The platform 124 shown in FIG. 1 iterates through the geodata data structure. The spatial analysis and planning tool 130 shown in FIG. 1 can assign the weights to each aspatial parameter. The platform 124 shown in FIG. 1 can generate the atmospheric corrosivity scale parameter.

At 403, a grid with cells representing each of the plurality of geospatial locations and the corresponding atmospheric corrosivity scale parameters is created. In this exemplary embodiment, the platform 124 creates the grid 118 with cells shown in FIG. 1.

At 404, the grid is stored for output of at least a portion of the plurality of geospatial locations and the corresponding atmospheric corrosivity scale parameters overlaid on a geographic map. In this exemplary embodiment, the platform 124 stores the grid 118 for output 120 on the display device 122 shown in FIG. 1.

Exemplary Computer Systems

Figure 5:
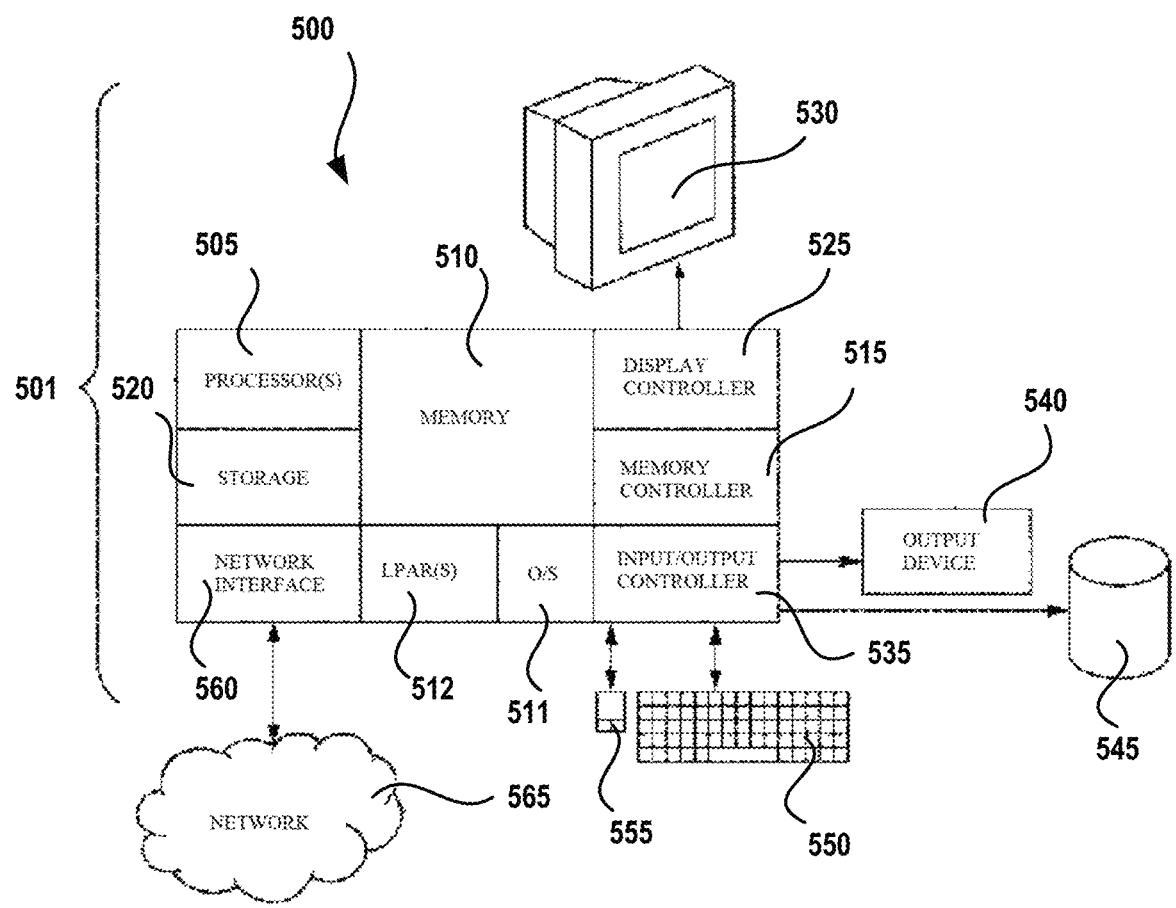
FIG. 5 is a schematic diagram for a computer system for implementing the subject matter of the subject disclosure.

Referring now to FIG. 5 with continuing reference to the forgoing figures, a computer system for generating an atmospheric corrosivity map is generally shown according to one or more embodiments. The methods described herein can be implemented in hardware, software (e.g., firmware), or a combination thereof. In an exemplary embodiment, the methods described herein are implemented in hardware as part of the microprocessor of a special or general-purpose digital computer, such as a personal computer, workstation, minicomputer, or mainframe computer. The system 500 therefore can include general-purpose computer or mainframe 501 capable of running multiple instances of an O/S simultaneously.

In an exemplary embodiment, in terms of hardware architecture, as shown in FIG. 5, the computer 501 includes one or more processors 505, memory 510 coupled to a memory controller 515, and one or more input and/or output (I/O) devices 540, 545 (or peripherals) that are communicatively coupled via a local input/output controller 535. The input/output controller 535 can be, for example but not limited to, one or more buses or other wired or wireless connections, as is known in the art. The input/output controller 535 can have additional elements, which are omitted for simplicity, such as controllers, buffers (caches), drivers, repeaters, and receivers, to enable communications. Further, the local interface can include address, control, and/or data connections to enable appropriate communications among the aforementioned components. The input/output controller 535 can include a plurality of sub-channels configured to access the output devices 540 and 545. The sub-channels can include fiber-optic communications ports.

The processor 505 is a hardware device for executing software, particularly that stored in storage 520, such as cache storage, or memory 510. The processor 505 can be any custom made or commercially available processor, a central processing unit (CPU), an auxiliary processor among several processors associated with the computer 501, a semiconductor based microprocessor (in the form of a microchip or chip set), a macroprocessor, or generally any device for executing instructions.

The memory 510 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 510 can incorporate electronic, magnetic, optical, and/or other types of storage media. Note that the memory 510 can have a distributed architecture, where various components are situated remote from one another, but can be accessed by the processor 505.

The instructions in memory 510 can include one or more separate programs, each of which comprises an ordered listing of executable instructions for implementing logical functions. In the example of FIG. 5, the instructions in the memory 510 a suitable operating system (OS) 511. The operating system 511 essentially controls the execution of other computer programs and provides scheduling, input-output control, file and data management, memory management, and communication control and related services. In accordance with one or more embodiments, the memory 510 and/or an I/O device 545 can be used to store the file attribute tables 126 and the data layers 128 shown in FIG. 1.

The memory 510 can include multiple logical partitions (LPARs) 512, each running an instance of an operating system. The LPARs 512 can be managed by a hypervisor, which can be a program stored in memory 510 and executed by the processor 505.

In an exemplary embodiment, a conventional keyboard 550 and mouse 555 can be coupled to the input/output controller 535. Other output devices such as the I/O devices 540, 545 can include input devices, for example but not limited to a printer, a scanner, microphone, and the like. Finally, the I/O devices 540, 545 can further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like.

The system 500 can further include a display controller 525 coupled to a display 530. In an exemplary embodiment, the system 500 can further include a network interface 560 for coupling to a network 565. The network 565 can be an IP-based network for communication between the computer 501 and any external server, client and the like via a broadband connection. The network 565 transmits and receives data between the computer 501 and external systems. In an exemplary embodiment, network 565 can be a managed IP network administered by a service provider. The network 565 can be implemented in a wireless fashion, e.g., using wireless protocols and technologies, such as WiFi, WiMax, etc. The network 565 can also be a packet-switched network such as a local area network, wide area network, metropolitan area network, Internet network, or other similar type of network environment. The network 565 can be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 501 is a PC, workstation, intelligent device or the like, the instructions in the memory 510 can further include a basic input output system (BIOS) (omitted for simplicity). The BIOS is a set of essential software routines that initialize and test hardware at startup, start the OS 511, and support the transfer of data among the hardware devices. The BIOS is stored in ROM so that the BIOS can be executed when the computer 501 is activated.

When the computer 501 is in operation, the processor 505 is configured to execute instructions stored within the memory 510, to communicate data to and from the memory 510, and to generally control operations of the computer 501 pursuant to the instructions.

In accordance with one or more embodiments described herein, the computer 501 can implement and/or perform the disclosed subject matter. As shown, computer 501 can include instructions in memory 510 for performing Steps 201-206 shown in FIG. 2 and/or Steps 401-406 shown in FIG. 4. The platform host system 110 shown in FIG. 1 can be implemented as the computer 501 shown in FIG. 5 with the display device 122 being implemented as the display 530 shown in FIG. 5.

The disclosed subject matter can be implemented as a system, a method, and/or a computer program product at any possible technical detail level of integration. The computer program product can include a computer readable storage medium (or media) having computer readable program instructions thereon for causing a processor to carry out embodiments and features of the subject disclosure.

The system can be implemented within a cloud environment. Cloud environments can be provided by a cloud services provider (i.e., "the cloud"). In such cloud environments, data resources can be abstracted among or across one or more computers and/or computer networks that make up the cloud. Examples of cloud computing environments include S3 by Amazon.com.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to exploit features of the present disclosure.

Embodiments and features of the subject disclosure are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the subject disclosure. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Supported Features and Embodiments

The detailed description provided above in connection with the appended drawings explicitly describes and supports various features of systems and methods for generating atmospheric corrosivity maps. By way of illustration and not limitation, supported embodiments include a computer-implemented method comprising: aggregating a plurality of disparate datasets into a geodata data structure specifying a plurality of geospatial locations and a set of aspatial parameters at each geospatial location, combining each aspatial parameter at each geospatial location to generate an atmospheric corrosivity scale parameter at each of the plurality of geospatial locations, creating a grid with cells representing each of the plurality of geospatial locations and each of the corresponding atmospheric corrosivity scale parameters, and storing the grid for output of at least a portion of the plurality of geospatial locations and the corresponding atmospheric corrosivity scale parameters overlaid on a geographic map.

Supported embodiments include the foregoing method, wherein the geodata data structure is selected from the group consisting of a database, a geodatabase, a shapefile, coverage, a raster image, a dbf table and a spreadsheet.

Supported embodiments include any of the foregoing methods, wherein the aspatial parameters include pollution, airborne salt content, and moisture.

Supported embodiments include any of the foregoing methods, wherein the aspatial parameters include sulfur dioxide pollution, chloride deposition and time of wetness.

Supported embodiments include any of the foregoing methods, wherein the plurality of disparate datasets are stored in data layers.

Supported embodiments include any of the foregoing methods, wherein the plurality of disparate datasets are stored on a server and accessed over a network.

Supported embodiments include any of the foregoing methods, wherein the aspatial parameters are combined to generate each corrosivity scale parameter using a predetermined formula.

Supported embodiments include any of the foregoing methods, wherein the combining step includes: iterating through the geodata data structure to assign weights to each aspatial parameter at each geospatial location, and generating a corrosivity scale parameter at each of the plurality of geospatial locations based upon the weight of each aspatial parameter at each of the plurality of geospatial locations.

Supported embodiments include an apparatus, a computer-readable storage medium, a system, a computer program product and/or means for implementing any of the methods or portions thereof.

Supported embodiments include a system comprising: a memory having computer readable instructions; and a processor for executing the computer readable instructions, the computer readable instructions including: aggregating a plurality of disparate datasets into a geodata data structure specifying a plurality of geospatial locations and a set of aspatial parameters at each geospatial location, combining each aspatial parameter at each geospatial location to generate an atmospheric corrosivity scale parameter at each of the plurality of geospatial locations, creating a grid with cells representing each of the plurality of geospatial locations and each of the corresponding atmospheric corrosivity scale parameters, and storing the grid for output of at least a portion of the plurality of geospatial locations and the corresponding atmospheric corrosivity scale parameters overlaid on a geographic map.

Supported embodiments include the foregoing system, wherein the geodata data structure is selected from the group consisting of a database, a geodatabase, a shapefile, coverage, a raster image, a dbf table and a spreadsheet.

Supported embodiments include any of the foregoing systems, wherein the aspatial parameters include pollution, airborne salt content, and moisture.

Supported embodiments include any of the foregoing systems, wherein the aspatial parameters include sulfur dioxide pollution, chloride deposition and time of wetness.

Supported embodiments include any of the foregoing systems, wherein the plurality of disparate datasets are stored in data layers.

Supported embodiments include any of the foregoing systems, wherein the plurality of disparate datasets are stored on a server and accessed over a network.

Supported embodiments include any of the foregoing systems, wherein the aspatial parameters are combined to generate each corrosivity scale parameter using a predetermined formula.

Supported embodiments include any of the foregoing systems, wherein the computer readable instructions include instructions for: iterating through the geodata data structure to assign weights to each aspatial parameter at each geospatial location, and generating a corrosivity scale parameter at each of the plurality of geospatial locations based upon the weight of each aspatial parameter at each of the plurality of geospatial locations.

Supported embodiments include an apparatus, a computer-readable storage medium, a computer-implemented method, a computer program product and/or means for implementing any of the foregoing systems or portions thereof.

Supported embodiments include a computer program product comprising a non-transitory computer readable storage medium having program instructions embodied therewith, the program instructions executable by processing circuitry to cause the processing circuitry to perform: aggregating a plurality of disparate datasets into a geodata data structure specifying a plurality of geospatial locations and a set of aspatial parameters at each geospatial location, combining each aspatial parameter at each geospatial location to generate an atmospheric corrosivity scale parameter at each of the plurality of geospatial locations, creating a grid with cells representing each of the plurality of geospatial locations and each of the corresponding atmospheric corrosivity scale parameters, and storing the grid for output of at least a portion of the plurality of geospatial locations and the corresponding atmospheric corrosivity scale parameters overlaid on a geographic map.

Supported embodiments include a computer-implemented method comprising: importing datasets having aspatial data corresponding to a plurality of geospatial locations from a plurality of data sources, storing the datasets in a plurality of file attribute tables with the aspatial data linked to the corresponding plurality of geospatial locations within the plurality of file attribute tables, aggregating a plurality of data layers from the plurality of file attribute tables to determine an atmospheric corrosivity scale parameter at each of the plurality of geospatial locations, creating a grid with cells representing each of the plurality of geospatial locations and the corresponding atmospheric corrosivity scale parameters, and storing the grid for output of at least a portion of the plurality of geospatial locations and the corresponding atmospheric corrosivity scale parameters overlaid on a geographic map.

Supported embodiments include a system comprising: a memory having computer readable instructions; and a processor for executing the computer readable instructions, the computer readable instructions including: importing datasets having aspatial data corresponding to a plurality of geospatial locations from a plurality of data sources, storing the datasets in a plurality of file attribute tables with the aspatial data linked to the corresponding plurality of geospatial locations within the plurality of file attribute tables, aggregating a plurality of data layers from the plurality of file attribute tables to determine an atmospheric corrosivity scale parameter at each of the plurality of geospatial locations, creating a grid with cells representing each of the plurality of geospatial locations and the corresponding atmospheric corrosivity scale parameters, and storing the grid for output of at least a portion of the plurality of geospatial locations and the corresponding atmospheric corrosivity scale parameters overlaid on a geographic map.

Supported embodiments include a computer program product comprising a non-transitory computer readable storage medium having program instructions embodied therewith, the program instructions executable by processing circuitry to cause the processing circuitry to perform: importing datasets having aspatial data corresponding to a plurality of geospatial locations from a plurality of data sources, storing the datasets in a plurality of file attribute tables with the aspatial data linked to the corresponding plurality of geospatial locations within the plurality of file attribute tables, aggregating a plurality of data layers from the plurality of file attribute tables to determine an atmospheric corrosivity scale parameter at each of the plurality of geospatial locations, creating a grid with cells representing each of the plurality of geospatial locations and the corresponding atmospheric corrosivity scale parameters, and storing the grid for output of at least a portion of the plurality of geospatial locations and the corresponding atmospheric corrosivity scale parameters overlaid on a geographic map.

Supported embodiments can provide various attendant and/or technical advantages in terms of an instrumentality that produces a corrosion risk assessment map specifically directed towards atmospheric corrosivity.

Supported embodiments include instrumentalities that combine various atmospheric properties to identify areas of high, medium, and low atmospheric corrosivity.

Supported embodiments include instrumentalities that provide companies with the ability to deploy resources in the most efficient manner and to specific areas of identifiable high corrosion risk.

The detailed description provided above in connection with the appended drawings is intended as a description of examples and is not intended to represent the only forms in which the present examples can be constructed or utilized.

It is to be understood that the configurations and/or approaches described herein are exemplary in nature, and that the described embodiments, implementations and/or examples are not to be considered in a limiting sense, because numerous variations are possible.

The specific processes or methods described herein can represent one or more of any number of processing strategies. As such, various operations illustrated and/or described can be performed in the sequence illustrated and/or described, in other sequences, in parallel, or omitted. Likewise, the order of the above-described processes can be changed.

Although the subject matter has been described in language specific to structural features and/or methodological acts, it is to be understood that the subject matter defined in the appended claims is not necessarily limited to the specific features or acts described above. Rather, the specific features and acts described above are presented as example forms of implementing the claims.

What is claimed is:

1. A computer-implemented method comprising:

receiving, by a platform host system, a sulfur dioxide pollution dataset corresponding to a plurality of geospatial locations from a first data source by a first interface, an airborne salt content dataset corresponding to a plurality of geospatial locations from a second data source by a second interface, and a weather dataset corresponding to a plurality of geospatial locations from a third data source by a third interface, wherein the platform host system communicates with the first interface, the second interface, and the third interface over an electronic network to receive the sulfur dioxide pollution dataset, the airborne salt content dataset, and the weather dataset from the first data source, the second data source, and the third data source;

aggregating, by the platform host system, the sulfur dioxide pollution dataset, the airborne salt content dataset, and the weather dataset into a geodata data structure specifying a plurality of geospatial locations and an aspatial sulfur dioxide pollution corrosion parameter, an aspatial airborne salt content corrosion parameter, and an aspatial time of wetness corrosion parameter at each geospatial location;

combining, by the platform host system, each aspatial corrosivity parameter at each geospatial location to generate a combined atmospheric corrosivity scale parameter at each of the plurality of geospatial locations, wherein the combined atmospheric corrosivity scale parameter is generated by assigning a first weight to the aspatial sulfur dioxide pollution corrosion parameter, a second weight to the aspatial airborne salt content corrosion parameter, and a third weight to the aspatial time of wetness corrosion parameter and combining the weighted aspatial corrosivity parameters at each of the plurality of geospatial location;

creating, by the platform host system, a grid with cells representing each of the plurality of geospatial locations and each of the corresponding combined atmospheric corrosivity scale parameters;

storing, by the platform host system, the grid for output of at least a portion of the plurality of geospatial locations and the corresponding atmospheric corrosivity scale parameters overlaid on a geographic map; and displaying the output on a display device in the form of an atmospheric corrosivity map to identify geographical areas of high, medium, and low atmospheric corrosivity.

2. The computer-implemented method of claim 1, wherein the geodata data structure is selected from the group consisting of a database, a geodatabase, a shapefile, coverage, a raster image, a dbf table and a spreadsheet.

3. A system comprising:

a platform host system having a memory having computer readable instructions; and a processor for executing the computer readable instructions, the computer readable instructions including:

receiving, by a platform host system, a sulfur dioxide pollution dataset corresponding to a plurality of geospatial locations from a first data source by a first interface, an airborne salt content dataset corresponding to a plurality of geospatial locations from a second data source by a second interface, and a weather dataset corresponding to a plurality of geospatial locations from a third data source by a third interface, wherein the platform host system communicates with the first interface, the second interface, and the third interface over an electronic network to receive the sulfur dioxide pollution dataset, the airborne salt content dataset, and the weather dataset from the first data source, the second data source, and the third data source;

aggregating, by the platform host system, the sulfur dioxide pollution dataset, the airborne salt content dataset, and the weather dataset into a geodata data structure specifying a plurality of geospatial locations and an aspatial sulfur dioxide pollution corrosion parameter, an aspatial airborne salt content corrosion parameter, and an aspatial time of wetness corrosion parameter at each geospatial location;

combining, by the platform host system, each aspatial corrosivity parameter at each geospatial location to generate a combined atmospheric corrosivity scale parameter at each of the plurality of geospatial locations, wherein the combined atmospheric corrosivity scale parameter is generated by assigning a first weight to the aspatial sulfur dioxide pollution corrosion parameter, a second weight to the aspatial airborne salt content corrosion parameter, and a third weight to the aspatial time of wetness corrosion parameter and combining the weighted aspatial corrosivity parameters at each of the plurality of geospatial location;

creating, by the platform host system, a grid with cells representing each of the plurality of geospatial locations and each of the corresponding combined atmospheric corrosivity scale parameters;

storing, by the platform host system, the grid for output of at least a portion of the plurality of geospatial locations and the corresponding atmospheric corrosivity scale parameters overlaid on a geographic map; and displaying the output on a display device in the form of an atmospheric corrosivity map to identify geographical areas of high, medium, and low atmospheric corrosivity.

4. The system of claim 3, wherein the geodata data structure is selected from the group consisting of a database, a geodatabase, a shapefile, coverage, a raster image, a dbf table and a spreadsheet.

5. A computer program product comprising a non-transitory computer readable storage medium having program instructions embodied therewith, the program instructions executable by processing circuitry to cause the processing circuitry to perform:

receiving, by a platform host system, a sulfur dioxide pollution dataset corresponding to a plurality of geospatial locations from a first data source by a first interface, an airborne salt content dataset corresponding to a plurality of geospatial locations from a second data source by a second interface, and a weather dataset corresponding to a plurality of geospatial locations from a third data source by a third interface, wherein the platform host system communicates with the first interface, the second interface, and the third interface over an electronic network to receive the sulfur dioxide pollution dataset, the airborne salt content dataset, and the weather dataset from the first data source, the second data source, and the third data source;

aggregating, by the platform host system, the sulfur dioxide pollution dataset, the airborne salt content dataset, and the weather dataset into a geodata data structure specifying a plurality of geospatial locations and an aspatial sulfur dioxide pollution corrosion parameter, an aspatial airborne salt content corrosion parameter, and an aspatial time of wetness corrosion parameter at each geospatial location;

combining, by the platform host system, each aspatial corrosivity parameter at each geospatial location to generate a combined atmospheric corrosivity scale parameter at each of the plurality of geospatial locations, wherein the combined atmospheric corrosivity scale parameter is generated by assigning a first weight to the aspatial sulfur dioxide pollution corrosion parameter, a second weight to the aspatial airborne salt content corrosion parameter, and a third weight to the aspatial time of wetness corrosion parameter and combining the weighted aspatial corrosivity parameters at each of the plurality of geospatial location;

creating, by the platform host system, a grid with cells representing each of the plurality of geospatial locations and each of the corresponding combined atmospheric corrosivity scale parameters;

storing, by the platform host system, the grid for output of at least a portion of the plurality of geospatial locations and the corresponding atmospheric corrosivity scale parameters overlaid on a geographic map; and displaying the output on a display device in the form of an atmospheric corrosivity map to identify geographical areas of high, medium, and low atmospheric corrosivity.

6. The computer program product of claim 5, wherein the geodata data structure is selected from the group consisting of a database, a geodatabase, a shapefile, coverage, a raster image, a dbf table and a spreadsheet.

* * * * *